United States Patent [19]

Stahly

[11] Patent Number: 5,008,425

[45] Date of Patent: *Apr. 16, 1991

[54] TRIFLUOROMETHYLATION OF CARBONYL COMPOUNDS

[75] Inventor: G. Patrick Stahly, Baton Rouge, La.

[73] Assignee: Ethyl Corporation, Richmond, Va.

[*] Notice: The portion of the term of this patent subsequent to Oct. 3, 2006 has been disclaimed.

[21] Appl. No.: 337,186

[22] Filed: Apr. 12, 1989

Related U.S. Application Data

[63] Continuation-in-part of Ser. No. 177,153, Apr. 4, 1988, abandoned, and a continuation-in-part of Ser. No. 196,680, May 20, 1988, Pat. No. 4,871,877.

[51] Int. Cl.$^5$ .......................... C07F 7/08; C07F 7/18; C07F 7/10
[52] U.S. Cl. .................................... 556/436; 556/418; 544/229; 549/215; 568/316; 568/326; 568/328; 568/348; 568/377
[58] Field of Search ................ 556/436, 118; 544/229; 549/215; 568/316, 326, 328, 348, 377

[56] References Cited

U.S. PATENT DOCUMENTS

| | | | |
|---|---|---|---|
| 2,920,092 | 1/1960 | Bailey | 260/448.2 |
| 3,472,888 | 10/1969 | Bazouin et al. | 260/448.8 |
| 4,210,596 | 7/1980 | Cella | 556/436 |
| 4,238,401 | 12/1980 | Cella et al. | 556/436 |
| 4,360,686 | 11/1982 | Wang et al. | 556/419 |
| 4,375,548 | 3/1983 | Wang et al. | 556/470 |
| 4,448,980 | 5/1984 | Sogah | 556/446 |
| 4,634,787 | 1/1987 | Wang | 556/470 |

OTHER PUBLICATIONS

Surya Prakash et al., *J. Am. Chem. Soc.*, 1989, 111, 393-395.
Fujita et al., *J. Am. Chem. Soc.*, 1985, 197, 4085-5087.
Yamazaki et al., *Chem. Abstracts*, 1986, 105, No. 190,436(d).

*Primary Examiner*—Paul F. Shaver
*Attorney, Agent, or Firm*—Richard J. Hammond; John F. Sieberth

[57] ABSTRACT

A process which comprises reacting under substantially anhydrous conditions a perfluoroalkyltrihydrocarbylsilane and a carbonyl compound in the presence of a catalyst such that the carbonyl compound is perfluoroalkylated.

13 Claims, No Drawings

TRIFLUOROMETHYLATION OF CARBONYL COMPOUNDS

REFERENCE TO RELATED APLICATIONS

This application is a Continuation-in-Part of prior co-pending applications Ser. No. 177,153, filed Apr. 4, 1988 and Ser. No. 196,680, filed May 20, 1988 now U.S. Pat. No. 4,871,877. Reference is also made to U.S. Pat. Nos. 4,804,772, 4,804,773, and 4,804,774 each of which issued Feb. 14, 1989 on applications filed by applicant herein on Apr. 4, 1988.

TECHNICAL FIELD

This invention relates in general to perfluoroalkylation of carbonyl compounds.

BACKGROUND

Early attempts to generate the trifluoromethide ion ($CF_3^-$) and trap it with electrophiles were unsuccessful. See for example, Hine, J. *Physical Organic Chemistry*, McGraw-Hill, New York, 1962, p 486; Haszeldine, R. N. *J. Chem. Soc.* 1954, 1273; Pierce, O. R., McBee, E. T.; Judd, G. F. *J. Am. Chem. Soc.* 9154, 76, 474; Bergman, E. *J. Org. Chem.* 1958, 23, 476.; McBee, E. T., Battershell, R. D., Braendlin, H. P. *J. Org. Chem.* 1963, 28, 1131. This was thought to be due to the rapid dissociation of $CF_3^-$ into $F^-$ and $CF_2$. Only recently reports have appeared describing the formal transfer of $CF_3^-$ to organic electrophiles in high yield. See Matsui, K., Tobita, E., Ando, M., Kondo, K. *Chem. Lett.* 1981, 1719; Ruppert, I., Schlich, K., Volbach, W., *Tetrahedron Lett.* 1984, 25, 2195; Burger, H., Grunwald, M., Pawelke, G. *J. Fluorine Chem.* 1986, 31, 89; Wakselman, C., Tordeaux, M. *Bull. Soc. Chim. Fr.* 1986, 868; Francese, C., Tordeux, M., Wakselman, C. *J. Chem. Soc., Chem. Commun.* 1987, 642; Francese, C., Tordeux, M., Kitazume, T., Ishikawa, N. *J. Am. Chem. Soc.* 1985, 107, 5186; Burton, D. J., Wiemers, D. M. *J. Am. Chem. Soc.* 1985, 107, 5014; Wiemers, D. M., Burton, D. J., *J. Am. Chem. Soc.* 1986, 108, 832.

Perfluoroalkyl aromatic compounds such as benzotrifluoride, 4-chlorobenzotrifluoride and 3-aminobenzotrifluoride are used in the production of a variety of products such as pharmaceuticals, crop protection chemicals, germicides, dyes, and the like. The classical method of forming trifluoromethyl aromatics involves the photochemical side-chain chlorination of a methyl aromatic compound to form a perchloromethyl substituted aromatic which in turn is reacted with hydrogen fluoride to effect an exchange of fluorine atoms for the chlorine atoms on the methyl group. Ortho- and para-trifluoromethylphenols and anilines are even more difficult to make. They have been synthesized by photochemical side-chain chlorination or bromination of the appropriate nitrotoluene to form the perhalomethyl nitrobenzene. This product is treated with hydrogen fluoride to form the perfluoromethyl nitrobenzene, which is then reduced to the perfluoromethyl aniline. Diazotization and hydrolysis of the latter forms the perfluoromethyl phenol.

In U.S. Pat. No. 4,634,787, Wang reports that reaction between trichloromethyltrimethylsilane and various carbonyl compounds using tetrabutylammonium fluoride as catalyst yielded trichloromethylated compounds as the product of the reaction. While the patentee refers to compounds having a $-CX_3$ group in which each X is independently halo, according to the patentee:

". . . preferably, each X is independently chloro or bromo. More preferably, each X is the same and is chloro or bromo. Even more preferably, each X is chloro. Preferred silanes [used as reactants in the process] are trichloromethylsilanes and the most preferred silane is trichloromethyltrimethylsilane."

The catalysts recommended by Wang for use in his process are KF, NaF, $CaF_2$ and $Bu_4NF$, the latter being his most preferred catalyst. Unfortunately $Bu_4NF$ is very expensive and difficult, if not impossible, to dry completely.

THE INVENTION

This invention provides a novel catalytic process by which perfluoroalkyl substituted compounds can be prepared by reaction of a perfluoroalkyltrihydrocarbyl silane and a carbonyl compound in the presence of a suitable catalyst.

More particularly, this invention provides a process for the synthesis of trifluoromethylated materials which comprises reacting a compound of the formula $CF_3SiR_3$ where R is alkyl or aryl with a carbonyl compound in the presence of a catalyst such that the carbonyl compound is trifluoromethylated. In accordance with one embodiment, the catalyst employed in this reaction is a metal salt such as KCN, KF, CsF, NaOH, $LiN_3$, or the like. In another embodiment, the catalyst is a nucleophilic material such as $R_3N$, $R_3P$, or the like.

Quinones represent one form of carbonyl compound which may be used in the practice of this invention. However, carbonyl compounds other than quinones can also be used in the process of this invention. These include aldehydes, ketones, anhydrides, imides, and the like.

This invention is in part based on the discovery that carbonyls may be perfluoroalkylated by means of perfluoroalkyltrihydrocarbyl silane using a variety of catalysts such as quaternary ammonium bifluorides, quaternary phosphonium bifluorides, alkali metal bifluorides, active alkali metal salts, certain trivalent phosphorus compounds, and aminopyridine compounds. In general quaternary amonium bifluorides, quaternary phosphonium bifluorides, alkali metal bifluorides are much less hygroscopic than the monofluorides such as $Bu_4NF$ and KF, and thus are much easier to use under the conditions of the process. At least some quaternary ammonium bifluorides are available at lower cost than $Bu_4NF$. What's more, potassium bifluoride is less expensive and more effective as a catalyst than potassium fluoride which must be used in stoichiometric or greater quantities in order to achieve reaction times of hours versus days. The reaction results in the perfluoroalkylation of the carbonyl compound used as the reactant.

In general, two broad classes of gem-disubstituted products can be produced by the process of this invention, the identity of the end product being determined by the presence or absence of a proton source in the reaction mixture. In the absence of a proton source the gem substituents are a perfluoroalkyl group and a trihydrocarbylsiloxy group. In the presence of a proton source the gem substituents are a perfluoroalkyl group and a hydroxyl group. For example, when using a quinone in the absence of a proton source the product is a gem-disubstituted cyclohexadienone in which the gem substituents are a perfluoroalkyl group and a trihydrocarbylsiloxy group. These gem-disubstituted compounds in turn can be readily converted to perfluoroalkyl substituted aromatics. Thus this invention circumvents the traditional need for photochlorination followed by halogen exchange using hydrogen fluoride as a means of preparing perfluoroalkyl aromatic compounds.

It is interesting to note that NaF and $CaF_2$, two of the fluoride ion catalysts recommended in U.S. Pat No. 4,634,787 for use as catalysts are ineffective as catalysts in the perfluoroalkylation process of this invention. On the other hand, potassium fluoride has been found to be an effective catalyst.

When conducting the process in the absence of a proton source, the process of this invention is conducted under essentially anhydrous conditions, preferably in a suitable liquid phase reaction medium. The preferred solvents or liquid reaction media for use in the process are dipolar aprotic solvents such as N,N-dimethylformamide, N,N-diethylformamide, N,N-dimethylacetamide, sulfolane, acetonitrile, hexamethylphosphoramide, nitrobenzene, dimethylsulfoxide, N-methylpyrrolidone, and the like. It is possible to perform the reaction in a substantially anhydrous aprotic solvent of low polarity such as tetrahydrofuran, 1,4-dioxane or the like.

A wide variety of bifluoride catalysts may be used in the practice of this invention. They may be represented by the general formula:

$$Q^+HF_2^-$$

where Q is a quaternary ammonium group, a quaternary phosphonium group or a alkali metal. Illustrative quaternary ammonium bifluorides include tetramethylammonium bifluoride, tetraethylammonium bifluoride, tetrabutylammonium bifluoride, cetyltrimethylammonium bifluoride, benzyltrimethylammonium bifluoride, and the like. Typical quaternary phosphonium bifluorides which may be employed include tetramethylphosphonium bifluoride, tetrathylphosphonium bifluoride, tetrabutylphosphonium bifluoride, decyltriethylphosphonium bifluoride, and the like. The alkali metal bifluorides are lithium bifluoride, sodium bifluoride potassium bifluoride, rubidium bifluoride and cesium bifluoride.

A mixture of two or more quaternary ammonium bifluorides or of two or more quaternary phosphonium bifluorides or of two or more alkali metal bifluorides may be used as the catalyst. Likewise, mixtures of one or more quaternary ammonium bifluorides with one or more quaternary phosphonium bifluorides and/or one or more alkali metal bifluorides can be used for this purpose, if desired. Similarly one may use a mixture of one or more quaternary phosphonium bifluorides with one or more alkali metal bifluorides as the catalyst.

The most preferred bifluoride catalysts are potassium bifluoride and tetraalkylammonium bifluorides in which each alkyl group contains up to about 18 carbon atoms. Reactions performed in acetonitrile using such catalysts have been found particularly efficacious.

Likewise, alkali metal salt catalysts may be used in the practice of this invention provided they exhibit the appropriate catalytic activity. In this connection, not all alkali metal salts exhibit a catalytic effect in the reaction and thus in any given instance where the suitability of a given alkali metal salt is not known, recourse should be had to the simple expedient of performing a few pilot experiments to determine whether the material will serve as a catalyst in the reaction.

Alkali metal salts which are active catalysts in the process of this invention include the alkali metal azides such as lithium azide, sodium azide, and potassium azide; alkali metal cyanides such as sodium cyanide, potassium cyanide, and cesium cyanide; alkali metal hydroxides such as sodium hydroxide and potassium hydroxide; alkali metal carbonates such as potassium carbonate and cesium carbonate; alkali metal fluorides such as potassium fluoride and cesium fluoride, and the like. The preferred salts in this category are devoid of fluorine.

The most preferred alkali metal salt catalysts are potassium cyanide and potassium carbonate, because of their high activity, ready availability, and low cost. Reactions performed in acetonitrile using potassium cyanide or potassium carbonate as the catalyst and in dimethylformamide with potassium carbonate as the catalyst have been found particularly efficacious.

Similarly, trihydrocarbylphosphites and hexahydrocarbyl phosphorous triamides can be used as catalysts in the process of this invention. Illustrative trihydrocarbylphosphites include trimethylphosphite, triethylphosphite, tripropylphosphite, triisopropylphosphite, tributylphosphite, tridodecylphosphite, triallylphosphite, trioleylphosphite, tricyclohexylphosphite, tricyclopropylcarbinylphosphite, triphenylphosphite, tritolylphosphite, tribenzylphosphite, phenyldiethylphosphite, dibenzyloctadecylphosphite, and the like. Among the hexahydrocarbylphosphorous triamides that may be employed as catalysts are hexamethylphosphorous triamide, hexaethylphosphorous triamide, hexapropylphosphorous triamide, hexaisopropylphosphorous triamide, hexabutylphosphorous triamide, hexacyclopentylphosphorous triamide, hexaphenylphosphorous triamide, hexa(4-ethylphenyl)phosphorous triamide, hexa(2-phenethyl)phosphorous triamide, hexacrotonylphosphorous triamide, and the like.

A mixture of two or more trihydrocarbylphosphites or of two or more hexahydrocarbylphosphorous triamides may be used as the catalyst. Likewise, mixtures of one or more trihydrocarbylphosphites with one or more hexahydrocarbylphosphorous triamides can be used for this purpose, if desired.

The most preferred trivalent phosphorus compounds used as catalysts are trialkylphosphites and hexaalkylphosphorous triamides in which each alkyl group contains up to about 18 carbon atoms. Reactions performed in acetonitrile using triethylphosphite or hexaethylphosphorous triamide as the catalyst have been found particularly efficacious.

Various aminopyridine compounds may be used as catalysts in the process of this invention. These include such compounds as 2-aminopyridine, 3-aminopyridine, 4-aminopyridine and fused ring analogs thereof such as 4-aminoquinaldine, 2,3-diaminopyridine, 2,6-diaminopyridine, 3,4-diaminopyridine, and alkyl derivatives of any of the foregoing such as 2-dimethylaminopyridine, 4-dimethylaminopyridine, 4-diethylaminopyridine, and the like. Aminopyrazine and aminopyrimidines such as 2-aminopyrimidine and 4,5-diaminopyrimidine may also be used as catalyst in the process.

A mixture of two or more aminopyridines may be used as the catalyst if desired.

The most preferred aminopyridine catalysts are the monoalkyl aminopyridines and the dialkylamino pryidines in which each alkyl group contains up to about 6 carbon atoms. Reactions performed in acetonitrile using 4-dimethylaminopyridine as the catalyst have been found particularly efficacious.

As noted above, perfluoroalkyl substituted compounds, namely gem-disubstituted compounds such as gem-disubstituted cyclohexadienones in which the gem substituents are a perfluoroalkyl group and a hydroxyl group, can be formed. These compounds are readily produced by reacting a carbonyl compound, e.g., a quinone, with a perfluoroalkyltrihydrocarbylsilane in the presence of an active catalyst of the type described above, and a proton source. The resultant gem-disubstituted compounds formed from quinones in turn can be readily converted to perfluoroalkyl substituted aromatics.

Carboxylic acids, water, alcohols, polyols, phenols, and the like exemplify the proton sources that may be used in the practice of the embodiments of this invention in which the gem-substituents are a hydroxyl group and a trihydrocarbylsiloxy group. The carboxylic acids may be cyclic (e.g., benzoic acid) or non-cyclic (e.g., acetic acid) and may be monocarboxylic acids (e.g., propionic acid) or polycarboxylic acids (e.g., succinic acid). Likewise, the alcohols may be cyclic (e.g., cyclohexanol) or non-cyclic (e.g., ethanol). The polyols may be linear (e.g., ethylene glycol) or branched (e.g., pentaerythritol). The phenols may be monohydric (e.g., phenol) or polyhydric (e.g., hydroquinone) and mononuclear (e.g., cresol) or polynuclear (e.g., 4,4'-dihydroxydiphenyl).

In selecting the catalyst-proton source for use in a given reaction, care should be taken to use substances which do not adversely interact with the another. For example, one should not employ a carboxylic acid promoter with alkali metal salts such as the carbonates, cyanides, hydroxides, or etc.

The amount of catalyst used (with or without a proton source) may be varied depending on the activity of the catalyst being used. Thus with some catalysts such as trihydrocarbylphosphites, hexahydrocarbylphosphorous triamides, aminopyridines, quaternary ammonium fluorides, quaternary ammonium bifluorides, and potassium carbonate, small catalytic quantities (e.g., as little as 0.10 mole per mole of carbonyl compound, e.g., quinone) may be used. With other catalysts such as KF, at least a stoichiometric amount relative to the carbonyl compound, e.g., quinone is desirable to achieve reasonable reaction rates (hours vs. days).

For best results when using a proton source, one should use a stoichiometric amount of the proton source relative to the quinone or other carbonyl compound present in the reaction mixture. Desirably the amount of excess proton source, if used, should be kept as small as convenient, typically no more than about 5 to 10 percent above stoichiometric.

Of the catalyst-proton source systems described above, systems based on the above-referred to alkali metal salts, especially potassium or cesium fluorides, along with carboxylic acids, especially the lower fatty acids (acetic acid, propionic acid) are preferred.

In accordance with a particularly preferred embodiment of this invention, the reaction is performed in the presence of ammonium bifluoride which serves both as the catalyst and as the proton source. Thus with this substance it is unnecessary to use an acid, alcohol, water, or the like as a proton source.

As noted above, when a proton source is used, this invention provides gem-disubstituted compounds in which the gem substituents are a perfluoroalkyl group and a hydroxyl group. In a preferred embodiment the perfluoroalkyl group is a trifluoromethyl group.

Among the preferred subclasses of compounds provided by this invention when employing a proton source are the cyclohexadienones which are formed when using a quinone as the carbonyl compound. Such cyclohexadienones are exemplified by the following:

4-hydroxy-4-trifluoromethyl-2,5-cyclohexadien-1-ones;
4-hydroxy-4-trifluoromethyl-2,5-cyclohexadien-1-ones having an alkyl substituent in at least the 2 or 6 position;
1,4-dihydro-4-hydroxy-1-oxo-4-trifluoromethylnaphthalenes;
9,10-dihydro-10-hydroxy-9-oxo-10-trifluoromethylanthracenes;
2-hydroxy-2-trifluoromethyl-2,4-cyclohexadien-1-ones;
2-hydroxy-2-trifluoromethyl-2,4-cyclohexadien-1-ones having an alkyl substituent in at least the 4 or 6 position; and
9,10-dihydro-10-hydroxy-9-oxo-10-trifluoromethylphenanthrenes.

Illustrative gem-disubstituted compounds include:
4-hydroxy-4-trifluoromethyl-2,5-cyclohexadien-1-one;
4-hydroxy-4-pentafluoroethyl-2,5-cyclohexadien-1-one;
4-heptafluoropropyl-4-hydroxy-2-methyl-2,5-cyclohexadien-1-one;
2,5-dimethyl-4-hydroxy-4-trifluoromethyl-2,5-cyclohexadien-1-one;
4-hydroxy-4-nonafluorobutyl-2,5-cyclohexadien-1-one;
2-ethyl-4-hydroxy-4-trifluoromethyl-2,5-cyclohexadien-1-one;
2,4-dihydroxy-4-trifluoromethyl-2,5-cyclohexadien-1-one;
4-hydroxy-4-trifluoromethyl-2-methoxy-2,5-cyclohexadien-1-one;
4-hydroxy-4-trifluoromethyl-2,5-dimethoxy-2,5-cyclohexadien-1-one;
2-anilino-4-hydroxy-4-pentafluoroethyl-2,5-cyclohexadien-1-one;
2-hydroxy-2-trifluoromethyl-3,5-cyclohexadien-1-one;
6-ethyl-2-hydroxy-2-trifluoromethyl-3,5-cyclohexadien-1-one;
4,6-diethyl-2-hydroxy-2-trifluoromethyl-3,5-cyclohexadien-1-one;
1,4-dihydro-4-hydroxy-1-oxo-4-trifluoromethyl-4-naphthalene;
1,4-dihydro-4-hydroxy-2-methyl-1-oxo-4-trifluoromethylnaphthalene;
9,10-dihydro-10-hydroxy-9-oxo-10-pentafluoroethylanthracene;
1,4-diamino-9,10-dihydro-10-hydroxy-9-oxo-10-pentafluoroethylanthracene;
9,10-dihydro-1,2,10-trihydroxy-9-oxo-10-pentafluoroethylanthracene;
9,10-dihydro-10-hydroxy-9-oxo-10-pentafluoroethylphenanthrene; and
9,10-dihydro-1-ethoxy-10-hydroxy-9-oxo-10-pentafluoroethyl-phenanthrene.

It is not known how or why the catalysts function in the process of this invention. Nor, is the structure or composition of the actual catalytic species known. All that is known is that when the catalyst is added to the reaction system in the form of a compound of the type referred to above the reaction proceeds. In the absence of the catalyst, no reaction occurs.

Ordinarily the catalytic processes of this invention (with or without a proton source) will be conducted at temperatures within the range of about −20 to about 100° C., although temperatures outside this range may be found useful in particular cases. Preferably, the temperature is maintained within the range of about 0 to about 25° C. throughout substantially the entire reaction period.

Quinones that may be used in the process of this invention include mononuclear and polynuclear quinones, both 1,2-quinones and 1,4-quinones. Electron donating substituents, such as hydrocarbyl groups, hydrocarbyloxy groups, amino and mono-and dihydrocarbylamino groups, the hydroxyl group, and the like may be present in the quinones. A few exemplary quinones which may be used include 1,2-benzoquinone, 1,4-benzoquinone, 2-methyl-1,4-benzoquinone, 2-methoxy-1,4-benzoquinone, 2,5-dimethoxy-1,4-benzoquinone, 2-anilino-1,4-benzoquinone, 2,5-dianilino-1,4-benzoquinone, 2-phenyl-1,4-benzoquinone, polyporic acid, the ubiquinones, 2,3-dimethyl-1,4-benzoquinone, 2,5-dimethyl-1,4-benzoquinone, 1,4-naphthoquinone, 1,2-naphthoquinone, Vitamin $K_1$, Vitamin $K_2$, 2-methyl-1,4-naphthoquinone, anthraquinone, 2-methylanthraquinone, 2-ethylanthraquinone, 2-tert-butylanthraquinone, 1-aminoanthraquinone, 2-aminoanthraquinone, 1-amino-4-hydroxyanthraquinone, 1,2-diaminoanthraquinone, 1,4-diaminoanthraquinone, 1,5-diaminoanthraquinone, 2,6-diaminoanthraquinone, 1,8-diamino-4,5-dihydroxyanthraquinone, 1-hydroxy-4-(p-toluidino)-anthraquinone, diphenoquinone, indanthrene blue, 1,2-dihydroxyanthraquinone, 9,10-phenanthraquinone, indanthrene violet, chrysophanic acid, and the like. Ketones and aldehydes that may be used in the process of this invention may be represented by the formula:

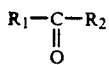

where $R_1$ is a hydrocarbyl group such as alkyl, aryl, etc., and $R_2$ is a hydrogen atom or a hydrocarbyl group such as alkyl, aryl, etc. Illustrative compounds of this type include benzaldehyde, paramethoxybenzaldehyde, tolualdehyde, propionaldehyde, acetone, methylisobutylketone, benzophenone, and the like. Other carbonyl compounds that may be used in the process include anhydrides, imides, polyketones, ketoesters, and the like. Not all carbonyl compounds will react in accordance with the process of this invention. However, the suitability of any given carbonyl compound can be readily determined by the simple expedient of running an experiment of the type referred to in the examples hereinafter.

The perfluoroalkyltrihydrocarbyl silanes used in the process of this invention may be represented by the general formula:

where R′ is a perfluoroalkyl group (trifluoromethyl, pentafluoroethyl, perfluorohexyl, etc.) and R, independently, is a hydrocarbyl group (alkyl, alkenyl, alkynyl, cycloalkyl, aryl, aralkyl, etc.). The number of carbon atoms in R and R′ is irrelevant so long as the silane is co-reactive with the carbonyl compound in the process. A few illustrative silane compounds include trifluoromethyltrimethylsilane, tridecyltrifluoromethylsilane, trifluoromethyltrivinylsilane, triallyltrifluoromethylsilane, tricyclopentyltrifluoromethylsilane, tricyclopropylcarbinyltrifluoromethylsilane, trifluoromethyltriphenylsilane, trifluoromethyltri-(1-naphthyl)silane, tribenzyltrifluoromethylsilane, and corresponding and similar analogs containing the higher "homologous" perfluoroalkyl groups such as perfluoroethyl, perfluoropropyl, perfluoroisopropyl, perfluorobutyl, etc.

As noted above, this invention also provides gem-disubstituted cyclohexadienones in which the gem substituents are a perfluoroalkyl group and a trihydrocarbylsiloxy group. In one preferred embodiment the perfluoroalkyl group is a trifluoromethyl group. In another preferred embodiment the trihydrocarbylsiloxy group is a trialkylsiloxy group. Particularly preferred compounds are those in which the gem substituents are a trialkylsiloxy group and a trifluoromethyl group.

Among the preferred subclasses of compounds provided by this invention are the following:

4-trialkylsiloxy-4-trifluoromethyl-2,5-cyclohexadien-1-ones;

4-trialkylsiloxy-4-trifluoromethyl-2,5-cyclohexadien-1-ones having an alkyl substituent in at least the 2 or 6 position;

1,4-dihydro-1-oxo-4-trialkYlsiloxy-4-trifluoromethylnaphthalenes;

9,10-dihydro-9-oxo-10-trialkylsiloxy-10-trifluoromethylanthracenes;

2-trialkylsiloxy-2-trifluoromethyl-2,4-cyclohexadien-1-ones;

2-trialkylsiloxy-2-trifluoromethyl-2,4-cyclohexadien-1-ones having an alkyl substituent in at least the 4 or 6 position; and 9,10-dihydro-9-oxo-10-trialkylsiloxy-10-trifluoromethylphenanthrenes.

Illustrative gem-disubstituted compounds of the type include:

4-trifluoromethyl-4-trimethylsiloxy-2,5-cyclohexadien-1-one;

4-pentafluoroethyl-4-trimethylsiloxy-2,5-cyclohexadien-1-one;

4-heptafluoropropyl-4-trimethylsiloxy-2,5-cyclohexadien-1-one;

4-tricyclohexylsiloxy-4-trifluoromethyl-2,5-cyclohexadien-1-one;

4-trifluoromethyl-4-triphenylsiloxy-2,5-cyclohexadien-1-one;

4-nonafluorobutyl-4-(4-biphenylyl)siloxy-2,5-cyclohexadien-1-one;

4-tribenzylsiloxy-4-trifluoromethyl-2,5-cyclohexadien-1-one;

2-ethyl-4-trifluoromethyl-4-tributylsiloxy-2,5-cyclohexadien-1-one;

4-trifluoromethyl-2-methoxy-4-trioctylsiloxy-2,5-cyclohexadien-1-one;

4-trifluoromethyl-2,5-dimethoxy-4-tri-(4-methylphenyl)siloxy-2,5-cyclohexadien-1-one;

2-anilino-4-pentafluoroethyl-4-trimethylsiloxy-2,5-cyclohexadien-1-one;

2-trifluoromethyl-2-triisopropylsiloxy-3,5-cyclohexadien-1-one;

6-ethyl-2-trifluoromethyl-2-tributylsiloxy-3,5-cyclohexadien-1-one;

4,6-diethyl-2-trifluoromethyl-2-triphenylsiloxy-3,5-cyclohexadien-1-one;

1,4-dihydro-1-oxo-4-trifluoromethyl-4-trioctylsiloxynaphthalene;

1,4-dihydro-2-methyl-1-oxo-4-trifluoromethyl-4-tripropylsiloxynaphthalene;

9,10-dihydro-9-oxo-10-pentafluoroethyl-10-triethylsiloxyanthracene;

1,4-diamino-9,10-dihydro-9-oxo-10-pentafluoroethyl-10-triethylsiloxyanthracene;

9,10-dihydro-1,2-dihydroxy-9-oxo-10-pentafluoroethyl-10-triethylsiloxyanthracene:

9,10-dihydro-9-oxo-10-pentafluoroethYl-10-triethYl-siloxyphenanthrene; and 9,10-dihydro-1-ethoxy-9-oxo-10-pentafluoroethyl-10-triethylsiloxyphenanthrene.

The practice and advantages of this invention will become still further apparent from the following illustrative examples. Examples I and II illustrate the preparation of perfluoroalkyltrihydrocarbylsilanes, the class of reactants used in the process of this invention.

EXAMPLE I

Triethyltrifluoromethylsilane

A flask equipped with a dry ice condenser was flame dried under a nitrogen stream, and charged with 25g (0.17 mol) of chlorotriethylsilane and 40 mL of dichloromethane. After cooling the resulting solution to −78° C. and charging the condenser with dry ice and acetone, 40 mL (0.43 mol) of bromotrifluoromethane (Freon 13B1) that had been condensed into a graduated tube was warmed to room temperature and allowed to distill into the flask. The cold solution was treated dropwise with 66mL (0.24 mol) of hexaethylphosphorous triamide, allowed to stir at −78° C. for two hours, and allowed to stir at room temperature overnight. Low boiling components were then short path distilled into a cold (−78° C.) receiving flask at >1 torr with the pot temperature kept at <50° C. The distillate was further fractionated by removal of the dichloromethane (40–45° C. at atmospheric pressure) and short path distillation to give 22.0 g of 98% pure (69% yield) triethyltrifluoromethylsilane: bp 52–54° C. at 10 torr; $^1$H NMR (CDCl$_3$) δ 0.59–1.16 (m); $^{19}$F NMR (CDCl$_3$, relative to CFCl$_3$) −61.3 ppm (s); IR (neat) 2960, 2915, 2882, 1458, 1413, 1206, 1055, 1020, 734, 693 cm$^{-1}$; mass spectrum (70 eV) m/z (relative intensity) 115 (66, M-CF$_3$), 105 (46), 87 (85), 77 (100), 59 (56), 49 (41), 47 (37), 41 (38). Anal. Calcd. for C$_7$H$_{15}$F$_3$Si: C, 45.62; H, 8.20. Found: C, 47.53; H, 8.56.

EXAMPLE II

Tri-n-butyltrifluoromethylsilane

A flask equipped with a dry ice condenser was flame dried under a nitrogen sream, and charged with 5.0g (20 mmol) of chloro -tri-n-butylsilane and 10 mL of dichloromethane. After cooling the resulting solution to −78° C. and charging the condenser with dry ice and acetone, 6.2 mL (66 mmol) of bromotrifluoromethane (Freon 13B1) that had been condensed into a graduated tube was warmed to room temperature and allowed to distill into the flask. The cooling bath was removed and the mixture was allowed to warm to the temperature of the refluxing Freon (−59° C.). To this cold solution was added, dropwise, 8.0 mL (29 mmol) of hexaethylphosphorous triamide. The resulting solution was stirred at reflux for 1 hour. Removal of the condenser and continued stirring for 1 hour resulted in evaporation of excess Freon and warming of the solution to room temperature. Dilution with 30 mL of dichloromethane, water (three 30 mL portions) and 1N HCl (two 30 mL portions) washing, drying (MgSO$_4$), and concentration afforded a residue which was short path distilled to give 3.6g (64% yield) of tri-n-butyltrifluoromethylsilane: bp 53–58° C. at 0.5 torr; $^1$H NMR (CDCl$_3$) δ 0.60–1.10 (m, 5H), 1.10–1.56 (m, 4H); $^{19}$F NMR (CDCl$_3$, relative to CFCl$_3$) −61.6 ppm (s); IR (neat) 2956, 2925, 2872, 1214, 1058 cm$^{-1}$; mass spectrum (70 eV) m/z (relative intensity) 199 (30, M-CF$_3$), 143 (80), 105 (30), 101 (27), 87 (30), 77 (66), 63 (43), 59 (41), 55 (54), 47 (25), 43 (20), 41 (100). Anal. Calcd. for C$_{13}$H$_{27}$F$_3$Si: C, 58.16; H, 10.14. Found: C, 58.26; H, 10.09.

The following examples illustrate the perfluoroalkylation process of this invention.

EXAMPLE III

4-Triethylsiloxy-4-trifluoromethyl-2,5-cyclohexadien-1-one

A mixture of 83 mg (0.77 mmol) of 1,4-benzoquinone, 166 mg (0.9 mmol) of triethyltrifluoromethylsilane, and 1 mL of acetonitrile was treated with 22mg (0.077 mmol) of tetrabutylammonium bifluoride and stirred at 25.C for 30 minutes. Concentration of the mixture afforded a black oil which was purified by means of preparative thin layer chromatography (one 2 mm silica gel plate eluted with 50% dichloromethane-50% petroleum ether) to give 74 mg (33% yield) of 4-triethylsiloxy-4-tri-fluoromethyl-2,5-cyclohexadien-1-one.

EXAMPLE IV

4-Triethylsiloxy-4-trifluoromethyl-2,5-cyclohexadien-1-one

A mixture of 100 mg (1.3 mmol) of potassium bifluoride, 119 mg (1.1 mmol) of 1,4-benzoquinone, and 2 mL of acetonitrile was treated with 239 mg (1.3 mmol) of triethyltrifluoromethylsilane and stirred vigorously at room temperature for 2 hours. The mixture was filtered and the filter cake was washed with dichloromethane. Concentration of the combined filtrates gave a black oil which was dissolved in dichloromethane and loaded onto a column of silica gel. The column was washed with dichloromethane until the eluent contained no uV active material. Concentration of the eluent gave a colorless oil which was purified by PTLC (one 2 mm silica gel plate eluted with 50% dichloromethane-50% petroleum ether) to give 134 mg (41% yield) of 4-triethylsiloxy-4-trifluoromethyl-2,5-cyclohexadien-1-one.

EXAMPLE V

4-Triethylsiloxy-4-trifluoromethyl-2,5-cyclohexadien-1-one

A mixture of 165 mg (1.5 mmol) of 1,4-benzoquinone, 332 mg (18 mmol) of triethyltrifluoromethylsilane, 15 mg (0.31mmol) of sodium cyanide, and 2 mL of acetonitrile was stirred vigorously at 25° C. for 42 hours. The mixture was filtered and the filtrate was concentrated in vacuo. Purification of the resulting residue by preparative thin layer chromatography (one 2 mm silica gel plate eluted with 50% dichloromethane - 50% petroleum ether) afforded 178 mg (41% yield) of 4-triethylsiloxy-4-trifluoromethyl-2,5-cyclohexadien-1-one as a pale yellow liquid: bp 68-78° C. at 0.5 torr; $^1$H NMR (CDCl$_3$) δ 0.40-1.06 (m, 15H), 6.41 (d, 2H, J=9 Hz), 6.89 (d, 2H, J=9 Hz); $^{19}$F NMR (CDCl$_3$, relative to CFCl$_3$) −83.8 ppm (t, J$_{FH}$=4 Hz); IR (neat) 2956, 2912, 2877, 1677, 1611, 12.65, 12.40, 1182, 1129, 1067, 1004, 835, 749, 732 cm$^{-1}$; mass spectrum (70 eV) m/z (relative intensity) 263 (6, M-C$_2$H$_5$), 139 (79), 111 (100) 105 (68), 83 (41), 77 (100), 47 (31), 45 (35). Anal. Calcd. for C$_{13}$H$_{19}$F$_3$O$_2$Si: C, 53.39; H, 6.54. Found: C, 53.60; H, 6.79.

EXAMPLE VI

4-Triethylsiloxy-4-trifluoromethyl-2,5-cyclohexadien-1-one

The procedure of Example V was repeated except that the catalyst was 293 mg (4.5 mmol) of potassium cyanide and the reaction period was but one hour. The 4-triethylsiloxy-4-tri-fluoromethyl-2,5-cyclohexadien-1-one was recovered in 64% yield.

EXAMPLE VII

4-Triethylsiloxy-4-trifluoromethyl-2,5-cyclohexadien-1-one

A mixture of 83 mg (0.77 mmol) of 1,4-benzoquinone, 1.66 mg (0.90 mmol) of triethyltrifluoromethylsilane, 92 mg (2.3 mmol) of powdered sodium hydroxide, and 1 mL of acetonitrile was stirred at 25° C. for 2 hours. The reaction mixture was poured into 20 mL of water and the resulting aqueous mixture was extracted with two 5 mL portions of dichloromethane. Combination, drying (MgSO$_4$), and concentration of the organic layers afforded a residue which was purified by PTLC, giving 66 mg (29% yield) of 4-triethyl-siloxy-4-trifluoromethyl-2,5-cyclohexadien-1-one.

EXAMPLE VIII

4-Triethylsiloxy-4-trifluoromethyl-2,5-cyclohexadien-1-one

A mixture of 83 mg (0.77 mmol) of 1,4-benzoquinone, 166 mg (0.90 mmol) of triethyltrifluoromethylsilane, 113 mg (2.3 mmol) of ground lithium azide, and 1 mL of acetonitrile was stirred at 25° C. for 22 hours. The reaction mixture was poured into 20 mL of 1N HCl and the resulting aqueous mixture was extracted with three 10 mL portions of dichloromethane. Combination, drying (MgSO$_4$), and concentration of the organic layers afforded a residue which was purified by PTLC, giving 96 mg (43% yield) of 4-triethyl-siloxy-4-trifluoromethyl-2,5-cyclohexadien-1-one.

EXAMPLE IX

4Triethylsiloxy-4-trifluoromethyl-2,5-cyclohexadien-1-one

The procedure of Example V was repeated using a mixture of 86 mg (0.80 mmol) of 1,4-benzoquinone, 147 mg (0.80 mmol) of triethyltrifluoromethylsilane, 22 mg (0.16 mmol) of potassium carbonate, and 1 mL of acetonitrile at 25.C for 7 hours. PTLC afforded 120 mg (51% yield) of 4-triethylsiloxy-4-trifluoromethyl-2,5-cyclohexadien-1-one.

EXAMPLE X

4-Triethylsiloxy-4-trifluoromethyl-2,5-cyclohexadien-1-one

The procedure of Example VIII was repeated using a mixture of 86 mg (0.80 mmol) of 1,4-benzoquinone, 147 mg (0.80 mmol) of triethyltrifluoromethylsilane, 22 mg (0.16 mmol) of potassium carbonate, and 1 mL of N,N-dimethylformamide at 25° C. for 1 hour. Extraction of the aqueous mixture with diethylether and PTLC afforded 123 mg (53% yield) of 4-triethylsiloxy-4-trifluoromethyl 2,5-cyclohexadien-1-one was achieved.

EXAMPLE XI 2,6-Di-tert-butyl-4-Triethylsiloxy-4-trifluoromethyl-2,5-cyclohexadien-1-one The procedure of Example V was repeated using a mixture of 176 mg (0.80 mmol) of 2,6-di-tert-butyl-1,4-benzoquinone, 147 mg (0.80 mmol) of triethyltrifluoromethylsilane, 22 mg (0.16 mmol) of potassium carbonate, and 1 mL of N,N-dimethylformamide at 25° C. for 21.5 hours. PTLC afforded 133 mg (41% yield) of 2,6-di-tert-butyl-4-triethylsiloxy-4-trifluoromethyl-2,5-cyclohexadien-1-one as a colorless liquid: $^1$H NMR (CDCl$_3$) δ 0.39-1.10 (m, 15H), 1.22 (s, 18H), 650 (s, 2H); $^{19}$F NMR (CDCl$_3$, relative to CFCl$_3$) −80.5 ppm (s); IR (neat) 2957, 2910, 2876, 1670, 1648, 1457, 1364, 1333, 1272, 1255, 1178, 1151, 1070, 1033, 994, 880, 845, 747 cm$^{-1}$; mass spectrum (70 eV) m/z (relative intensity 375 (60, M-C$_2$H$_5$), 335 (50), 299 (20), 57 (100) 41 (40). Anal. Calcd. for C$_{21}$H$_{35}$F$_3$O$_2$Si: C, 62.34; H, 8.72. Found: C, 63.05; H, 8.75.

EXAMPLE XII 4,6-Di-tert-butyl-2-triethylsiloxy-2-trifluoromethyl-3,5-cyclohexadien-1-one The procedure of Example V was repeated using a mixture of 176 mg (0.80 mmol) of 3,5-di-tert-butyl-1,2-benzoquinone, 147 mg (0.80 mmol) of triethyltrifluoromethylsilane, 22 mg (0.16 mmol) of potassium carbonate, and 1 mL of acetonitrile at 25 C for 24 hours. PTLC afforded 269 mg (83% yield) of 4,6-di-tert-butyl-2-triethylsiloxy-2-trifluoromethyl-3,5-cyclohexadien-1-one as a yellow liquid: $^1$H NMR (CDCl$_3$) δ 0.35-1.10 (m, 15H), 1.16 (s, 3H), 1.23 (s, 3H), 5.85 (d, 1H, J=2 Hz), 6.84 (d, 1H, J=2 Hz); $^{19}$F NMR (CDCl$_3$, relative to CFCl$_3$) −80.0 ppm (s); IR (neat) 2955, 2909, 2874, 1689, 1459, 1366, 1270, 1244, 1179, 1143, 1072, 1033, 998, 890, 831, 810, 743, 695 cm$^{-1}$; mass spectrum (70 eV) m/z (relative intensity) 404 (29, M+), 389 (20), 375 (79, M-C$_2$H$_5$), 57 (100). Anal. Calcd. for C$_{21}$H$_{35}$F$_3$O$_2$Si: C, 62.34; H, 8.72. Found: C, 62.46; H, 8.69.

EXAMPLE XIII 1,4-Dihydro-1-oxo-4-triethylsiloxy-4-trifluoromethylnaphthalene

The procedure of Example X was repeated using a mixture of 127 mg (0.80 mmol) of 1,4-naphthoquinone, 147 mg (0.80 mmol) of triethyltrifluoromethylsilane, 22 mg (0.16 mmol) of potassium carbonate, and 1 mL of N,N-dimethylformamide at 25 C for 2 hours. PTLC afforded 113 mg (41% yield) of 1,4-dihydro-1-oxo-4-triethyl-siloxy-4-trifluoromethylnaphthalene as a brown liquid: $^1$H NMR (CDCl$_3$) δ 0.30-1.00 (m, 15H), 6.65 (d, 1H, J=10 Hz), 7.06 (d, 1H, J=10 Hz), 7.50-8.30 (m, 4H); $^{19}$F NMR (CDCl$_3$, relative to CFCl$_3$) −79.6 ppm (s); IR (neat) 2956, 2911, 2876, 1676, 1599, 1454, 1379, 1299, 1253, 1178, 1154, 1110, 1065, 1058, 1018, 952, 836, 767, 748, 732 cm$^{-1}$; mass spectrum (70 eV) m/z (relative intensity) 313 (40, M-C$_2$H$_5$), 189 (55), 161 (100), 133 (55), 77 (30). Anal. Calcd. for C$_{17}$H$_{21}$F$_3$O$_2$Si: C, 59.62; H, 6.18. Found: C, 59.91; H, 6.33.

EXAMPLE XIV 9,10-Dihydro-9-oxo-10-triethylsiloxy-10-trifluoromethylanthracene The procedure of Example X was repeated using a mixture of 167 mg (0.80 mmol) of 9,10-anthraquinone, 147 mg (0.80 mmol) of triethyltrifluoromethylsilane, 22 mg (0.16 mmol) of potassium carbonate, and 2 mL of N,N-dimethylformamide at 25.C for 5 hours. PTLC afforded 258 mg (82% yield) of 9,10-dihydro-9-oxo-10-tri-ethylsiloxy-10-trifluoromethylanthracene as a colorless liquid: $^1$H NMR (CDCl$_3$) δ 0.19–0.90 (m, 15H), 7.50–7.90 (m, 4H), 7.90–8.13 (m, 2H), 8.30–8.47 (m, 2H); $^{19}$F NMR (CDCl$_3$, relative to CFCl$_3$) −79.9 ppm (s) (t, J$_{FH}$=14 Hz); IR (neat) 2959, 2931, 2875, 1667, 1589, 1455, 1412, 1320, 1272, 1245, 1179, 1134, 1087, 1012, 959, 932, 893, 841, 817, 763, 736, 715, 692, 662, 630, 596 cm$^{-1}$; mass spectrum (70 eV) m/z (relative intensity) 363 (10, M-C$_2$H$_5$), 211 (100), 183 (25), 77 (35). Anal. Calcd. for C$_{21}$H$_{23}$F$_3$O$_2$Si: C, 64.26; H, 5.91. Found: C, 64.26; H, 6.01.

EXAMPLE XV 9,10-Dihydro-9-oxo-10-triethylsiloxy-10-trifluoromethylphenanthrene The procedure of Example X was repeated using a mixture of 167 mg (0.80 mmol) of 9,10-phenanthrenequinone, 147 mg (0.80 mmol) of triethyltrifluoromethylsilane, 22 mg (0.16 mmol) of potassium carbonate, and 2 mL of N,N-dimethylformamide at 25 C for 4 hours. PTLC afforded 260 mg (83% yield) of 9,10-dihydro-9-oxo -10-triethylsiloxy-10-trifluoromethylphenanthrene as a pale yellow liquid: $^1$H NMR (CDCl$_3$) δ 0.45–1.17 (m, 15H), 7.31–8.10 (m, 8H); $^{19}$F NMR (CDCl$_3$, relative to CFCl$_3$) −79.4 ppm (s); IR (neat) 2953, 2909, 2874, 1707, 1598, 1450, 1298, 1279, 1251, 1230, 1178, 1117, 1029, 1009, 944, 918, 837, 778, 766, 757, 731, 630 cm$^{-1}$; mass spectrum (70 eV) m/z (relative intensity) 363 (49, M-C$_2$H$_5$), 294 (100), 236 (29). Anal. Calcd. for C$_{21}$H$_{23}$F$_3$O$_2$Si: C, 64.26; H, 5.91. Found: C, 64.28; H, 5.92.

EXAMPLE XVI

4-Tributylsiloxy-4-trifluoromethyl-2,5-cyclohexadien-1-one

A mixture of 86 mg (0.80 mmol) of 1,4-benzoquinone, 215 mg (0.80 mmol) of tri-n-butyltrifluoromethylsilane, 22 mg (0.16 mmol) of ground potassium carbonate, and 1 mL of N,N-dimethylformamide was stirred vigorously at room temperature for one hour and poured into 10 mL of 1N HCl. The resulting aqueous mixture was extraced with three 10 mL portions of diethyl ether. Combination, drying (MgSO$_4$), and concentration of the ether layers afforded a residue which was purified by PTLC (one 2 mm silica gel plate eluted with 25% dichloromethane - 75% petroleum ether) to give 156 mg (52% yield) of 4-tri-n-butylsiloxy-4-trifluoro -methyl-2,5-cyclohexadien-1-one: $^1$H NMR (CDCl$_3$) δ 0.50–0.61 (m, 6H); 0.85 (t, 9H, J=5 Hz), 1.19–1.35 (m, 12H), 6.39 (d, 2H, J=9 Hz), 6.82 (d, 2H, J=9 Hz); $^{19}$F NMR (CDCl$_3$, relative to CFCl$_3$) −80.0 ppm (s); IR (KBr) 2960, 2920, 2870, 2865, 1692, 1680, 1640, 1380, 1265, 1240, 1180, 1130, 1080, 1065, 1005, 990, 835, cm$^{-1}$; mass spectrum (70 eV) m/z (relative intensity) 319 (5, M-C$_4$H$_9$), 307 (48), 161 (20), 139 (39), 121 (52), 111 (75), 105 (62), 93 (72), 83 (29), 77 (100), 65 (24), 63 (50), 61 (24), 55 (68), 44 (31), 43 (35), 41 (35). Anal. Calcd. for C$_{19}$H$_{31}$F$_3$O$_2$Si: C, 60.60; H, 8.30. Found: C, 60.76; H, 8.43.

EXAMPLE XVII

4-Triethylsiloxy-4-trifluoromethyl-2,5-cyclohexadien-1-one

A mixture of 83 mg (0.77 mmol) of 1,4-benzoquinone, 1.66 mg (0.90 mmol) of triethyltrifluoromethylsilane, and 1 mL of acetonitrile was treated with one drop of hexaethylphosphorous triamide, stirred at 25 C for 23.5 hours, and poured into 20 mL of water. The resulting aqueous mixture was extracted with three 10 mL portions of dichloromethane. Combination, drying (MgSO$_4$), and concentration of the organic layers afforded a residue which was purified by preparative thin layer chromatography (one 2 mm silica gel plate developed with 50% dichloromethan—50% petroleum ether), giving 142 mg (63% yield) of 4-triethylsiloxy -4-trifluoromethyl-2,5-cyclohexadien-1-one as an amber liquid: $^1$H NMR (CDCl$_3$) δ 0.40–1.06 (m, 15H), 6.41 (d, 2H, J=9 Hz), 6.89 (d, 2H, J=9 Hz); $^{19}$F NMR (CDCl$_3$, relative to CFCl$_3$) −83.8 ppm (t, J$_{FH}$=4 Hz); IR (neat) 2956, 2912, 2877, 1677, 1611, 1265, 1240, 1182, 1129, 1067, 1004, 835, 749, 732 cm$^{-1}$; mass spectrum (70 eV) m/z (relative intensity) 263 (6, M-C$_2$H$_5$), 139 (79), 111 (100), 105 (68), 83 (41), 77 (100), 47 (31), 45 (35). Anal. Calcd. for C$_{13}$H$_{19}$F$_3$O$_2$Si: C, 53.39; H, 6.54. Found: C, 53.60; H, 6.79.

EXAMPLE XVIII

4-Triethylsiloxy-4-trifluoromethyl-2,5-cyclohexadien-1-one

The procedure of Example XVII was repeated except that 26 μL (0.15 mmol) of triethylphosphite was used in place of hexaethylphosphorous triamide, the reaction time was 21 hours, and the reaction mixture was simply concentrated in vacuo to give a residue which was purified by PTLC to give 115 mg (51% yield) of 4-triethylsiloxy-4-trifluoromethyl-2,5-cyclohexadien-1-one.

EXAMPLE XIX

4-Triethylsiloxy-4-trifluoromethyl-2,5-cyclohexadien-1-one

A mixture of 86 mg (0.80 mmol) of 1,4-benzoquinone, 147 mg (0.80 mmol) of triethyltrifluoromethylsilane, 5 mg (0.04 mmol) of 4-dimethylaminopyridine, and 1 mL of acetonitrile was stirred at 25° C. overnight and concentrated in vacuo. The resulting residue was purified by preparative thin layer chromatography (one 2 mm silica gel plate eluted with 50% dichloromethane-50% petroleum ether), to give 116 mg (50% yield) of 4-triethylsiloxy -4-trifluoromethyl-2,5-cyclohexadien-1-one as an amber liquid: $^1$H NMR (CDCl$_3$) δ 0.40–1.06 (m, 15H), 6.41 (d, 2H, J=9 Hz), 6.89 (d, 2H, J=9 Hz); $^{19}$F NMR (CDCl$_3$, relative to CFCl$_3$) −83.8 ppm (t, J$_{FH}$=4 Hz); IR (neat) 2956, 2912, 2877, 1677, 1611, 1265, 1240, 1182, 1129, 1067, 1004, 835, 749, 732 cm$^{-1}$; mass spectrum (70 eV) m/z (relative intensity) 263 (6, M-C$_2$H$_5$), 139 (79), 111 (100), 105 (68), 83 (41), 83 (41), 77 (100), 47

(31), 45 (35). Anal. Calcd. for $C_{13}H_{19}F_3O_2Si$: C, 53.39; H, 6.54. Found: C, 53.60; H, 6.79.

EXAMPLE XX

4-Triethylsiloxy-4-trifluoromethyl-2,5-cyclohexadien-1-one

The procedure of Example XIX was repeated with the exception that the temperature was maintained at 0–5° C. and the reaction time was 3 hours. The yield of 4-triethylsiloxy -4-trifluoromethyl-2,5-cyclohexadien-1-one was 55%.

Other compounds of this invention can be readily produced by procedures similar to those described in the above examples. For example, by substituting 2,6-di-tert-butyl-1,4-benzoquinone for 1,4-benzoquinone, the product is 2,6-di-tert-butyl-4-triethyl -siloxy-4-trifluoromethyl-2,5-cyclohexadien-1-one. Similarly, use of 1,2-benzoquinone in lieu of 1,4-benzoquinone results in the formation of 3,5-di-tert-butyl-2-triethylsiloxy-2-trifluoro -methyl-3,5-cyclohexadien-1-one. Likewise, with use of 1,4-naphthoquinone as the quinone reactant in the above procedures, the product formed is 1,4-dihydro-1-oxo-4-triethyl -siloxy-4-trifluoromethylnaphthalene. When anthraquinone is employed as the reactant in this illustrative reaction, the product is 9,10-dihydro-9-oxo-10-triethylsiloxy-10-trifluoromethylanthracene. And, by using the general procedures of Examples III and IV as applied to phenanthrenequinone, the product is 9,10-dihydro-9-oxo-10-triethylsiloxy-10-trifluoromethylphenanthrene. When tri-n-butyltrifluoromethylsilane is used in place of triethyltrifluoromethylsilane in the procedures of Examples III and IV, 4-tri-n-butylsiloxy-4-trifluoromethyl -2,5-cyclohexadien-1-one is formed.

EXAMPLE XXI

1-Phenyl-1-triethylsiloxy-2,2,2-trifluoroethane

A mixture of 65 mg (1.1 mmol) of dry KF (dried at 200° C. and 25 mm Hg for three days), 0.5 mL of CH3CN, 30 L (0.30 mmol) of benzaldehyde (PhCHO) and 68 mg (0.37 mmol) of Et3SiCF3 was vigorously stirred at room temperature for 19 hours. A portion of the reaction mixture was partitioned between 1N HCl and diethyl ether. GC of the diethyl ether solution showed three peaks with one major product. A portion of the product was subjected to GC/MS analysis which indicated that the products (in order of most to least abundant) were 1-phenyl-1-triethylsiloxy-2,2,2-trifluoroethane, 1-phenyl-2,2,2-trifluoroethanol, (Et3Si)2O, and an unknown.

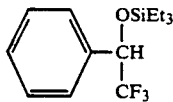

EXAMPLE XXII

1-Phenyl-1-triethylsiloxy-2,2,2-trifluoroethane

A mixture of 650 mg (11 mmol) of dry KF (dried at 200° C. and 25 mm Hg overnight), 0.5 mL of CH3CN (dried over molecular sieves), and 300μL (3.0 mmol) of benzaldehyde was treated with 680 mg (3.7 mmol) of Et3SiCF3. The mixture became warm, but cooled to room temperature after a few minutes. It was allowed to stir overnight. The mixture was then filtered and the filter cake washed with 1 mL of acetonitrile. GC of the filtrate resembled that of the solution formed in Example XXI. The solvent was removed by rotary evaporation. The residue was loaded on to a column of 10 g of silica gel (flash grade) packed in petroleum ether. The column was eluted with 100 mL petroleum ether to give a first fraction, then with 100 mL 50% petroleum ether/50% dichloromethane to give a second fraction. These two fractions were stripped, fraction one yielding 642.7 mg of colorless liquid, and fraction two, 76.2 mg of colorless liquid. GC analysis of fraction one showed that the major reaction product therein was 1-phenyl-1-t riethylsiloxy-2,2,2,-trifluoroethane. GC/MS confirmed the presence of 1-phenyl-1-triethylsiloxy-2,2,2,-trifluoroethane. Fraction two exhibited many peaks including unreacted benzaldehyde and 1-phenyl-2,2,2-trifluoroethanol.

EXAMPLE XXIII

1-Triethylsiloxy-1-trifluoromethylcyclohexane

A mixture of 260 mg (4.5 mmol) of KF (dried at 180° C. and 25 mm Hg for two weeks), 155μL (1.5 mmol) of cyclohexanone, 313 mg (1.7 mmol) of Et3SiCF3 and 3 mL of acetonitrile was stirred at room temperature. The reaction mixture was inspected by GC at selected intervals. After one hour GC indicated that the reaction mixture contained 7% of 1-triethylsiloxy-1-trifluoromethylcyclohexane. After two hours the content of this product was indicated to be 16%. After 3.5 hours the reaction mixture was indicated to contain 20% of this product.

EXAMPLE XXIV 1,5-Dihydro-2-triethylsiloxy-2-trifluoromethyl-5-oxofuran

A mixture of 65 mg (1.1 mmol) of KF (dried at 190° C. and 25 mm Hg overnight), 29 mg (0.30 mmol) of maleic anhydride, 68 mg (0.37 mmol) of Et3SiCF3 and 0.5 mL of acetonitrile was stirred at room temperature for one hour. The reaction mixture was red in color. The reaction mixture was filtered and the filtrate subjected to GC/MS analysis which showed the presence of a small quantity (trace) of 1,5-dihydro-2-triethylsiloxy-2-trifluoro -methyl-5-oxofuran (originally misidentified as 2-triethylsiloxy -5-trifluoromethyoxy furan).

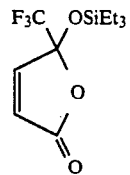

EXAMPLE XXV 1,5-dihydro-1-phenyl-2-triethylsiloxy-2-trifluoromethyl-5-oxopyrrole A mixture of 65 mg (1.1 mmol) of KF (dried at 190° C. and 25 mm Hg for several days), 52 mg (0.30 mmol) of N-phenymaleimide, 68 mg (0.37 mmol) of Et3SiCF3 and 0.5 mL of acetonitrile was stirred at room temperature for twenty three hours. The reaction mixture, which was red in color, was filtered and the filtrate subjected to GC/MS analysis. The product mixture was indicated to contain a small quantity (trace) of 1,5-dihydro-1-phenyl-2-tri -ethylsiloxy-2-trifluoromethyl-5- oxopyrrole (originally misidentified as 1-phenyl-2-triethylsiloxy-5-trifluoromethoxy pyrrole).

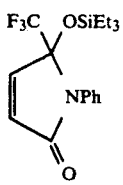

EXAMPLE XXVI (Phenyl)(α-triethylsiloxy-α-trifluoromethylbenzyl)ketone

To a mixture of 260 mg (4.5 mmol) of KF (dried at 180° C. and 25 mm Hg for about two weeks), 315 mg (1.5 mmol) of benzil, and 5 mL of acetonitrile supported in a room temperature water bath was added 429 mg of 73% $Et_3SiCF_3$ (1.7 mmol). The yellow reaction mixture was stirred vigorously and after a few minutes the bath was removed. Within 15 minutes the mixture suddenly became warm (not hot) to the touch and changed from yellow to red-orange in color. After one hour the product was subjected to GC analysis, which showed the absence of benzil. The reaction mixture was filtered and the white solids washed with dichloromethane. The filtrates were stripped to give a red oil. This was placed on two 2 mm silica plates and developed with a 50/50 volume percent mixture of petroleum ether and dichloromethane. A first fraction was composed of 517.7 mg of colorless liquid which was indicated to be 99% pure by GC. A second fraction was composed of 134.4 mg of a crystalline solid which exhibited two peaks indicating a mixture of two products in a ratio 76% to 24%. These fractions were subjected to GC/MS analyses. The first fraction was shown to be composed of (phenyl)(α-triethylsiloxy-α-trifluoromethylbenzyl)ketone:

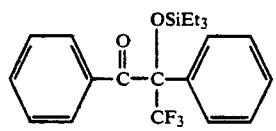

Comparative Examples A and B presented below indicate that two of the fluorine containing catalysts recommended by Wang as effective in the reactions described in U.S. Pat. No. 4,634,787 are ineffective in the reactions of this invention.

COMPARATIVE EXAMPLE A

Attempted Use of Sodium Fluoride as Catalyst

A mixture of 83 mg (0.77 mmol) of 1,4-benzoquinone, 166 mg (0.90 mmol) of triethyltrifluoromethylsilane, and 1 mL of acetonitrile was treated with 97 mg (2.3 mmol) of sodium fluoride (dried at 180° C., 25 torr overnight) and stirred vigorously at room temperature for 3 days. A gas chromatographic analysis showed that no reaction occurred.

COMPARATIVE EXAMPLE B

Attempted Use of Calcium Fluoride as Catalyst

A mixture of 46 mg (0.4 mmol) of benzoquinone, 92 mg (0.5 mmol) of triethyltrifluoromethylsilane, 102 mg (1.3 mmol) of calcium fluoride, and 1 mL of acetonitrile was stirred at room temperature for 1 hour. A gas chromatographic analysis showed no reaction occurred The novel gem-disubstituted cyclohexadienones produced by this invention are eminently useful in the synthesis of a wide variety of perfluroalkyl substituted aromatic compounds, many of which are themselves novel and of considerable utility. For example, the gem-disubstituted cyclohexadienones can be reduced using suitable metal reductant systems to perfluoroalkylated phenols. Likewise, the cyclohexadienones can be subjected to reductive amination to produce perfluoroalkylated aromatic amines. Procedures useful in effecting such reductions and reductive aminations are illustrated in Examples XXVII through XXXII below.

EXAMPLE XXVII

4-Trifluoromethylphenol

A solution of 300 mg (1.0 mmol) of 4-triethylsiloxy-4-trifluomethyl-2,5-cyclohexadien-1-one in 1 mL of absolute ethanol was treated successively with 134 mg (2.0 mmol) of zinc dust and 1 mL of a solution of 80% acetic acid - 20% water. The mixture was heated to reflux in a 120±5° C. oil bath for one hour, allowed to cool to room temperature, and poured into 10 mL of water. The resulting aqueous mixture was extracted with three 10 mL portions of diethyl ether. Combination, drying ($MgSO_4$), and concentration of the ether layers afforded a residue which was subjected to PTLC (one 2 mm plate eluted with 20% petroleum ether - 80% dichloromethane). Removal of the UV-active band from the plate afforded a mixture of triethylsilanol (23 area percent by gas chromatography) and 4-trifluoromethylphenol (71 area percent by gas chromatography): mass spectrum (70 eV) m/z (relative intensity) 162 (100, M+), 143 (56), 112 (31), 39 (22).

EXAMPLE XXVIII 2,6-Di-tert-butyl-4-trifluoromethylphenol

A strip of aluminum foil weighing 264 mg (9.8 mmol) was amalgamated by immersion in a solution of 2% mercuric chloride in water for 15 seconds, washed with absolute ethanol followed by diethyl ether, cut into small pieces, and added to a solution of 412 mg of 96% pure (0.98 mmol) 2,6-di-tert-butyl-4-triethyl -siloxy-4-trifluoromethyl-2,5-cyclohexadien-1-one in 25 mL of 10% water—90% tetrahydrofuran. The resulting mixture was heated at 70° C. for 1.5 hours, allowed to cool to room temperature, and filtered. The filter cake was washed with tetrahydrofuran. Concentration of the combined filtrates gave a residue which was poured into 25 mL of water. The aqueous mixture was extracted with three 10 mL portions of dichloromethane. Combination drying ($MgSO_4$), and concentration of the organic layers gave a residue which was purified by PTLC (one 2 mm silica gel plate eluted with petroleum ether), affording 247 mg of 95% pure (87% yield) 1,6-di-tert-butyl-4-trifluoromethylphenol. An analytical sample obtained by crystallization from methanol: mp 78–80° C.; $^1H$ NMR ($CDCl_3$) δ 1.45 (s, 18H), 5.56 (broad s, 1H), 7.50 (s, 1H); $^{19}F$ NMR ($CDCl_3$, relative to $CFCl_3$) −61.7 ppm (s); IR (KBr) 3632, 2963, 1337, 1319, 1241, 1167, 1141, 1109, 893, 668 $cm^{-1}$; mass spectrum (70 eV) m/z (relative intensity) 274 (20, M+), 259 (100), 231 (28), 57 (57), 41 (54). Anal. Calcd. for $C_{15}H_{21}F_3O$: C, 65.67; H, 7.72. Found: C, 65.46; H, 7.94.

EXAMPLE XXIX

2,4-Di-tert-butyl-6-trifluoromethylphenol

A strip of aluminum foil weighing 267 mg (9.9 mmol) was amalgmated by immersion in a solution of 2% mercuric chloride in water for 15 seconds, washed with absolute ethanol followed by diethyl ether, cut into small pieces, and added to a solution of 400 mg (0.99 mmol) of 4,6-di-tert-butyl-2-triethylsiloxy-2-trifluoromethyl-3,5-cyclohexadien-1-one in 25 mL of 10% water -90% tetrahydrofuran. The resulting mixture was heated at 70° C. for 1.5 hours, allowed to cool to room temperature, and filtered. The filter cake was washed with 10 mL of tetrahydrofuran. Concentration of the combined filtrates gave a residue which was poured into 25 mL of water. The aqueous mixture was extracted with three 10 mL portions of dichloromethane. Combination, drying and concentration of the organic layers gave a residue which was purified by PTLC (one 2 mm silica gel plate eluted with petroleum ether), affording 226 mg (83% yield) of 2,4-di-tert-butyl-6-trifluoromethylphenol as a colorless liquid: $^1$H NMR (CDCl$_3$) δ 1.31 (s, 9H), 1.45 (s, 9H), 5.56 (q, H, $J_{HF}$=4 Hz), 7.39 (d, 1H, J=2 Hz), 7.54 (d, 1H, J=2 Hz); IR (neat) 3624, 2959, 2906, 2868, 481, 1458, 1448, 1363, 1340, 1263, 1251, 1170, 1126, 1097, 887, 694 cm$^{-1}$; mass spectrum (70 eV) m/z (relative intensity) 274 (20, M+), 259 (100), 239 (68), 98 (20), 57 (22), 41 (34).

EXAMPLE XXX

4-Trifluoromethylphenol

A solution of 3.9 g (20 mmol) of 4-tri-n-butylsiloxy-4-trifluoromethyl-2,5-cyclohexadien-1-one in 10 mL of absolute ethanol was treated successively with 1.3 g (20 mmol) of zinc dust and 10 mL of a solution of 80% acetic acid - 20% water. The mixture was heated to reflux for one hour, allowed to cool to room temperature, and poured into 100 mL of water. The resulting aqueous mixture was extracted with three 50 mL portions of diethyl ether. Combination, drying (MgSO$_4$), and concentration of the ether layers afforded a residue which purified by short path distillation at 5.0 torr. At 60-65° C., 0.80 g (47% yield) of 4-trifluoromethylphenol was collected.

EXAMPLE XXXI

4-Trifluoromethyl-1-naphthol

A strip of aluminum foil weighing 278 mg (10 mmol) was amalgamated by immersion in a solution of 2% mercuric chloride in water for 15 seconds, washed with absolute ethanol followed by diethyl ether, cut into small pieces, and added to a solution of 353 mg (1.0 mmol) of 1,4-dihydro-1-oxo-4-triethylsiloxy-4-trifluoromethylnaphthalene in 10 mL of 10% water - 90% tetrahydrofuran. The resulting mixture was heated at 70 C for 1.5 hours, allowed to cool to room temperature, and filtered. The filter cake was washed with diethyl ether. Concentration of the combined filtrates gave a residue which was poured into 25 mL of water. The aqueous mixture was extracted with three 10 mL portions of dichloromethane. Combination, drying (MgSO$_4$), and concentration of the organic layers gave a residue which was purified by PTLC (one 2 mm silica gel plate eluted with dichloromethane), affording 190 mg (90% yield) of 4-trifluoromethyl-1-naphthol as a white solid. An analytical sample was obtained by recrystallization from dichloromethane-hexane: mp 132-133° C.; $^1$H NMR (CDCl$_3$) δ 5.50 (broad s, 1H), 6.79 (d, 1H, J=8 Hz), 7.50-7.80 (m, 3H), 8.10-8.45 (m, 2H); $^{19}$F NMR (CDCl$_3$, relative to CFCl$_3$) −59.5 ppm (s); IR (KBr) 3327, 1580, 1385, 1355, 1327, 1260, 1251, 1241, 1195, 1178, 1146, 1120, 1111, 1101, 1056, 767, cm$^{-1}$; mass spectrum (70 eV) m/z (relative intensity) 212 (100, M+), 133, (32), 115 (100). Anal. Calcd. for C$_{11}$H$_7$F$_3$O: C, 62.27; H, 3.33. Found: C, 61.82; H, 3.50.

EXAMPLE XXXII

4-Trifluoromethylaniline

A mixture of 400 mg (1.4 mmol) of 4-triethylsiloxy-4-trifluoromethyl-2,5-cyclohexadien-1-one, 572 mg (4.2 mmol) of ethyl glycinate hydrochloride, 298 mg (3.6 mmol) of sodium bicarbonate, and 10 mL of 95% ethanol was heated to reflux for 6 hours, allowed to cool to room temperature, and poured into 25 mL of water. The resulting aqueous mixture was extracted with three 10 mL portions of dichlormethane. The organic layers were combined and extracted with six 5 mL portions of 1N HCl. Combination of the aqueous layers and treatment with solid sodium bicarbonate until neutral to pH paper gave a cloudy mixture that was extracted with three 10 mL portions of dichloromethane. The organic layers were combined, dried (MgSO$_4$), and stripped to give a residue which was purified by PTLC (one 2 mm silica gel plate eluted with dichloromethane), affording 160 mg (73% yield) of 4-trifluoromethylaniline.

Orthohydrocarbyl perfluoroalkyl phenolic compounds such as 2-alkyl- and 2,6-dialkyl-4-perfluoroalkylphenols, 2-alkyl-4-perfluoroalkylnaphthols and 6-alkyl- and 4,6-alkyl-2-perfluoroalkylphenols may be used as antioxidants and stablizers in polymers, lubricants and like substrates normally susceptible to oxidative deterioration during storage or use, and as intermediates for the synthesis of phosphites, thiophosphites, phosphates, thiophosphates, and like products which may be used as antioxidants and as agricultural chemicals. Exemplary orthohydrocarbyl perfluoroalkyl phenolic compounds of this type include:

2-methyl-4-perfluoromethylphenol
2-ethyl-4-perfluoromethylphenol
2-isopropyl-4-perfluoromethylphenol
2-tert-butyl-4-perfluoromethylphenol
2-(2-octyl)-4-perfluoromethylphenol
2-benzyl-4-perfluoromethylphenol
2-cyclopentyl-4-perfluoromethylphenol
2,6-dimethyl-4-perfluoromethylphenol
2,6-diethyl-4-perfluoromethylphenol
2,6-diisopropyl-4-perfluoromethylphenol
2,6-di-tert-butyl-4-perfluoromethylphenol
2-tert-butyl-6-methyl-4-perfluoromethylphenol
2-benzyl-6-methyl-4-perfluoromethylphenol
2-cyclopentyl-6-ethyl-4-perfluoromethylphenol
2-ethyl-4-perfluoroethylphenol
2-ethyl-4-perfluoropropylphenol
2-isopropyl-4-perfluoroethylphenol
2-tert-butyl-4-perfluoroethylphenol
2-(2-octyl)-4-perfluorobutylphenol
2,6-dimethyl-4-perfluoropentylphenol
2,6-diethyl-4-perfluoroethylphenol
2,6-diisopropyl-4-perfluoroisopropylphenol
2,6-di-tert-butyl-4-perfluoroethylphenol
2-tert-butyl-6-methyl-4-perfluorobutylphenol
2-methyl-4-perfluoromethylnaphthol
2-ethyl-4-perfluoromethylnaphthol
2-isopropyl-4-perfluoromethylnaphthol 2-tert-butyl-4-perfluoromethylnaphthol
2-(2-octyl)-4-perfluoromethylnaphthol
2-methyl-4-perfluoroethylnaphthol
2-ethyl-4-perfluoropropylnaphthol
2-isopropyl-4-perfluoroethylnaphthol
2-tert-butyl-4-perfluoroethylnaphthol
2-(2-octyl)-4-perfluorobutylnaphthol
2-benzyl-4-perfluoromethylnaphthol
2-cyclopentyl-4-perfluoromethylnaphthol
6-methyl-2-perfluoromethylphenol
6-ethyl-2-perfluoromethylphenol
6-isopropyl-2-perfluoromethylphenol
6-tert-butyl-2-perfluoromethylphenol
6-(2-decyl)-2-perfluoromethylphenol
6-benzyl-2-perfluoromethylphenol
6-cyclopentyl-2-perfluoromethylphenol
4,6-dimethyl-2-perfluoromethylphenol
4,6-diethyl-2-perfluoromethylphenol
4,6-diisopropyl-2-perfluoromethylphenol
4,6-di-tert-butyl-2-perfluoromethylphenol
40 4-tert-butyl-6-methyl-2-perfluoromethylphenol
4-benzyl-6-methyl-2-perfluoromethylphenol
4-cyclopentyl-6-ethyl-2-perfluoromethylphenol
4-ethyl-2-perfluoroethylphenol
4-ethyl-2-perfluoropropylphenol
4-isopropyl-2-perfluoroethylphenol
4-tert-butyl-2-perfluoroethylphenol
4-(2-dodecyl)-2-perfluorobutylphenol
4,6-dimethyl-2-perfluoropentylphenol
4,6-diethyl-2-perfluoroethylphenol
4,6-diisopropyl-2-perfluoroisopropylphenol
4,6-di-tert-butyl-2-perfluoroethylphenol
4-tert-butyl-6-methyl-2-perfluorobutylphenol Orthohydrocarbyl perfluoroalkyl aromatic amines such as 2-alkyl- and 2,6-dialkyl-4-perfluoroalkyl anilines, 2-alkyl-4-perfluoroalkyl-1-naphthyl amines, and 6-alkyl- and 4,6-dialkyl -2-perfluoroalkyl anilines are useful as intermediates for the synthesis of crop protection chemicals such as herbicides and plant growth regulants and as intermediates for the synthesis of pesticides such as insecticides, miticides, acaricides, and fungicides.

Exemplary orthohydrocarbyl perfluoroalkyl aromatic amines include:
2-methyl-4-perfluoromethylaniline
2-ethyl-4-perfluoromethylaniline
2-isopropyl-4-perfluoromethylaniline
2-tert-butyl-4-perfluoromethylaniline
2-(2-octyl)-4-perfluoromethylaniline
2-benzyl-4-perfluoromethylaniline
2-cyclopentyl-4-perfluoromethylaniline
2,6-dimethyl-4-perfluoromethylaniline
2,6-diethyl-4-perfluoromethylaniline
2,6-diisopropyl-4-perfluoromethylaniline
2,6-di-tert-butyl-4-perfluoromethylaniline
2-tert-butyl-6-methyl-4-perfluoromethylaniline
2-benzyl-6-methyl-4-perfluoromethylaniline
2-cyclopentyl-6-ethyl-4-perfluoromethylaniline
2-ethyl-4-perfluoroethylaniline
35 2-ethyl-4-perfluoropropylaniline
2-isopropyl-4-perfluoroethylaniline
2-tert-butyl-4-perfluoroethylaniline
2-(2-octyl)-4-perfluorobutylaniline
2,6-dimethyl-4-perfluoropentylaniline
2,6-diethyl-4-perfluoroethylaniline
2,6-diisopropyl-4-perfluoroisopropylaniline
2,6-di-tert-butyl-4-perfluoroethylaniline
2-tert-butyl-6-methyl-4-perfluorobutylaniline
2-methyl-4-perfluoromethyl-1-naphthylamine
2-ethyl-4-perfluoromethyl-1-naphthylamine
2-isopropyl-4-perfluoromethyl-1-naphthylamine
2-tert-butyl-4-perfluoromethyl-1-naphthylamine
2-(2-octyl)-4-perfluoromethyl-1-naphthylamine
2-methyl-4-perfluoroethyl-1-naphthylamine
2-ethyl-4-perfluoropropyl-1-naphthylamine
2-isopropyl-4-perfluoroethyl-1-naphthylamine
2-tert-butyl-4-perfluoroethyl-1-naphthylamine
2-(2-octyl)-4-perfluorobutyl-1-naphthylamine
2-benzyl-4-perfluoromethyl-1-naphthylamine
2-cyclopentyl-4-perfluoromethyl-1-naphthylamine
6-methyl-2-perfluoromethylaniline
6-ethyl-2-perfluoromethylaniline
6-isopropyl-2-perfluoromethylaniline
6-tert-butyl-2-perfluoromethylaniline
6-(2-decyl)-2-perfluoromethylaniline
6-benzyl-2-perfluoromethylaniline
6-cyclopentyl-2-perfluoromethylaniline
4,6-dimethyl-2-perfluoromethylaniline
4,6-diethyl-2-perfluoromethylaniline
4,6-diisopropyl-2-perfluoromethylaniline
4,6-di-tert-butyl-2-perfluoromethylaniline
4-tert-butyl-6-methyl-2-perfluoromethylaniline
4-benzyl-6-methyl-2-perfluoromethylaniline
4-cyclopentyl-6-ethyl-2-perfluoromethylaniline
4-ethyl-2-perfluoroethylaniline
4-ethyl-2-perfluoropropylaniline
4-isopropyl-2-perfluoroethylaniline
4-tert-butyl-2-perfluoroethylaniline
4-(2-dodecyl)-2-perfluorobutylaniline
4,6-dimethyl-2-perfluoropentylaniline
4,6-diethyl-2-perfluoroethylaniline
4,6-diisopropyl-2-perfluoroisopropylaniline
4,6-di-tert-butyl-2-perfluoroethylaniline
4-tert-butyl-6-methyl-2-perfluorobutylaniline Still other products which may be produced from the gem-dicyclohexadienones of this invention include (i) novel gem-disubstituted cyclohexadienones in which the gem-substitutents are a perfluoroalkyl group and a hydroxyl group, (ii) novel gem-disubstituted cyclohexanones in which the gem-substituents are a perfluoroalkyl group and a trihydrocarbylsiloxy group, (iii) novel gem-disubstituted cyclohexanols in which the gem-substituents are a perfluoroalkyl group and a trihydrocarbylsiloxy group, and (iv) novel gem-disubstituted cyclohexanones in which the gem-substituents are a perfluoroalkyl group and a hydroxyl group. Methods for effecting the synthesis of such compounds are illustrated in Examples XI through XX below.

EXAMPLE XXXIII

4-Hydroxy-4-trifluoromethyl-2,5-cyclohexadien-1-one

A mixture of 200 mg (0.68 mmol) of 4-triethylsiloxy-4-trifluoromethyl-2,5-cyclohexadien-1-one and 1 mL of a solution of 1 part 37% hydrochloric acid in 9 parts absolute ethanol was heated at reflux overnight and poured into 10 mL of water. The resulting aqueous mixture was extracted with three 10 mL portions of dichloromethane. Combination, drying (MgSO$_4$), and concentration of the organic layers afforded a residue which was purified by PTLC (one 2 mm silica gel plate eluted with 1% methanol—99% dichloromethane) to give 109 mg (89% yield) of 4-hydroxy-4-trifluoromethyl-2,5-cyclohexadien-1-one. An analytical sample was obtained by crystallization from dichloromethane-hexane: mp 84–86° C.; $^1$H NMR (CDCl$_3$) δ 3.40 (broad s, 1H), 6.40 (d, 2H, J=10 Hz), 6.89 (d, 2H, J=10 Hz); $^{13}$C NMR (CDCl$_3$) 70.2 (q, J$_{CF}$=30 Hz), 125. 0 (q, J$_{CF}$=286H), 132.2 (d), 142. 7 (d), 184.5 (s) ppm; $^{19}$F NMR (CDCl$_3$) relative to CFCl$_3$) −79.6 ppm (s); IR (KBr) 3374, 3105, 3022, 2919, 1693, 1671, 1632, 1620, 1396, 1249, 1235, 1195, 1174, 1089, 1078, 1003, 988, 980, 973, 863, 698 cm$^{-1}$; mass spectrum (70 eV) m/z (relative intensity) 178 (5, M$^{30}$), 109 (100), 81 (34), 53 (36). Anal. Calcd. for C$_7$H$_5$F$_3$O$_2$: C, 47.20; H, 2.83. Found: C, 47.42; H, 2.80.

In Examples XXXIV through XLII procedures as described in Example XI were used.

EXAMPLE XXXIV

4-Hydroxy-4-trifluoromethyl-2,5-cyclohexadien-1-one

From 300 mg (0.80 mmol) of 4-tri-n-butylsiloxy-4-tri-fluoromethyl-2,5-cyclohexadien-1-one was obtained a product mixture. Gas chromatographic/mass spectral analysis showed that the major component of this mixture was 4-hydroxy-4-trifluoro-methyl-2,5-cyclohexadien-1-one.

EXAMPLE XXXV 2.6-Di-tert-butyl-4-hydroxy-4-trifluoromethyl-2,5-cyclohexadien-1-one From 350 mg (0.87 mmol) of 2,6-di-tert-butyl-4-triethyl-siloxy-4-trifluoromethyl-2,5-cyclohexadien-1-one was obtained a product mixture which was purified by PTLC (one 2 mm silica gel plate eluted with dichloromethane) to give 245 mg (98% yield) of 2,6-di-tert-butyl-4-hydroxy-4-trifluoromethyl-2,5-cyclohexadien-1-one. An analytical sample was obtained by crystallization from hexane: mp 93–94° C.; $^1$H NMR (CDCl$_3$) δ 1.25 (s, 18H), 2.57 (s, 1H), 6.48 (s, 2H); $^{19}$F NMR (CDCl$_3$ relative to CFCl$_3$) −79.8 to −79.9 ppm (m); IR (KBr) 3374, 3103, 3022, 2919, 1693, 1671, 1632, 1620, 1396, 1249, 1235, 1195, 1174, 1089, 1078, 1003, 988, 980, 973, 863, 698 cm$^{-1}$; mass spectrum (70 eV) m/z (relative intensity) 290 (7, M+), 275 (18), 247 (20), 57 (100), 43 (35), 41 (62). Anal. Calcd. for C$_{15}$H$_{12}$F$_3$O$_2$: C, 62.05; H, 7.29. Found: C, 61.98; H, 7.46.

EXAMPLE XXXVI 4,6-Di-tert-butyl-2-hydroxy-2-trifluoromethyl-3,5-cyclohexadien-1-one From 350 mg (0.87 mmol) of 4,6-di-tert-butyl-2-triethyl-siloxy-2-trifluoromethyl-3,5-cyclohexadien-1-one was obtained a product mixture which was purified by PTLC (one 2 mm silica gel plate eluted with 20% dichloromethane - 80% petroleum ether) to give 218 mg (87% yield) of 4,6-di-tert-butyl-2-hydroxy-2-tri-fluoromethyl-3,5-cyclohexadien-1-one. An analytical sample was obtained by crystallization from hexane: mp 58–61° C.; $^1$H NMR (CDCl$_3$) δ 1.17 (s, 9H), 1.25 (s, 9H), 4.32 (s, IH), 5.96 (d, 1H, J=2 Hz), 6.93 (d, 1H, J=2 Hz); $^{19}$F NMR (CDCl$_3$ relative to CFCl$_3$) −79.5 ppm (s); IR (KBr) 3456, 2964, 1676, 1372, 1367, 1254, 1234, 1217, 1186, 1163, 1151, 1124, 694 cm$^{-1}$; mass spectrum (70 eV) m/z (relative intensity) 290 (12, M+), 275 (20), 205 (28), 69 (30), 57 (100), 43 (27), 41 (77), 39 (20), Anal. Calcd. for C$_{15}$H$_{12}$F$_3$O$_2$: C, 62.05; H, 7.29. Found: C, 62.16; H, 7.27.

EXAMPLE XXXVII 9,10-Dihydro-10-hydroxy-9-oxo-10-trifluoromethylnaphthalene

From 350 mg (1.0 mmol) of 9,10-dihydro-9-oxo-10-triethyl-siloxy-10-trifluoromethylnaphthalene was obtained a product mixture which was purified by PTLC (one 2 mm silica gel plate eluted with 1% methanol - 99% dichloromethane) to give 192 mg of 89% pure (73% yield) 9,10-dihydro-10-hydroxy-9-oxo-10-trifluoromethylnaphthalene. An analytical sample was obtained by crystallization from dichloromethane hexane: mp 73–76° C.; $^1$H NMR (CDCl$_3$) δ 3.94 (s, 1H), 6.48 (d, 1H, J=10 Hz), 7.02 (d, 1H, J =10 Hz), 7.43–8.18 (m, 4H); $^{19}$F NMR (CDCl$_3$ relative to CFCl$_3$) −80.0 ppm (s); IR(KBr) 3368, 1667, 1627, 1597, 1454, 1377, 1301, 1283, 1230, 1188, 1172, 1156, 1142, 1102, 1047, 1017, 935, 838, 769, 754, 603, 560 cm$^{-1}$; mass spectrum (70 eV) m/z (relative intensity) 228 (8, M$^{30}$), 159 (100), 131 (30), 103 (22), 77 (25). Anal. Calcd. for C$_{11}$H$_7$F$_3$O$_2$: C, 57.90; H, 3.09. Found: C, 57.94; H, 3.12.

EXAMPLE XXXVIII 9.10-Dihydro-10-hydroxy-9-oxo-10-trifluoromethylanthracene

From 340 mg (0.89 mmol) of 9,10-dihydro-9-oxo-10-tri-ethylsilyolxy-10-trifluoromethylanthracene was obtained a product mixture which was purified by PTLC (one 2 mm silica gel plate eluted with dichloromethane) to give 223 mg (90% yield) of 9,10-dihydro-10-hydroxy-9-oxo-10-trifluoromethylanthracene. An analytical sample was obtained by crystallization from dichloro-methane-hexane: mp 153–155° C.; $^1$H NMR (CDCl$_3$) δ 3.56 (s, 1H), 7.47–7.82 (m, 4H), 7.92–8.31 (m, 4H); $^{19}$F NMR (CDCl$_3$ relative to CFCl$_3$) −79.8 ppm (s); IR (KBr) 3417, 1656, 1598, 1584, 1458, 1320, 1269, 1219, 1165, 1128, 1062, 933, 764, 716 cm$^{-1}$; mass spectrum (70 eV) m/z (relative intensity) 278 (1, M+), 209 (100), 152 (24). Anal. Calcd. for C$_{15}$H$_9$F$_3$O$_2$: C, 64.75; H, 3.26. Found: C, 64.63; H, 3.29.

EXAMPLE XXXIX 9,10-Dihydro-10-hydroxy-9-oxo-10-trifluoromethylohenanthrene

From 350 mg (0.89 mmol) of 9,10-dihydro-9-oxo-10-tri-ethylsiloxy-10-trifluoromethylphenanthrene was obtained a product mixture that was purified by PTLC (one 2mm slica gel plate eluted with 50% diohlorome-thane - 50% petroleum ether) to give 238 mg (96% yield) of 9,10-dihydro-10-hydroxy-9-oxo-10-trifluoromethylphenanthrene. An analytical sample was obtained by crystallization from dichloromethane-hexane: mp 148–151° C.; $^1$H NMR (CDCl$_3$) δ 4.76 (s, 1H), 7.22–8.07 (m, 8H); $^{19}$F NMR (CDCl$_3$ relative to CFCl$_3$) −78.5 ppm (s); IR (KBr) 3455, 1687, 1598, 1479, 1451, 1321, 1299, 1286, 1228, 1210, 1167, 1110, 1056, 1015, 956, 941, 905, 778, 758, 731, 641, 615 cm$^{-1}$; mass spectrum (70 eV) m/z (relative intensity) 278 (31, M+), 209 (100), 181 (43), 152 (34), 75 (33). Anal. Calcd. for C$_{15}$H$_9$F$_3$O$_2$: C, 64.75; H, 3.26. Found: C, 64.75; H, 3.30.

EXAMPLE XL

4-Triethylsiloxy-4-trifluoromethylcyclohexanone

A solution of 291 mg of 4-triethylsiloxy-4-trifluoro-methyl-2,5-cyclohexadien-1-one in 2 mL of absolute ethanol was treated with a few mg of 5% palladium on carbon, hydrogenated in a Parr shaker for one hour under 50 psig of hydrogen, and filtered. Concentration of the filtrate gave 4-triethylsiloxy-4-trifluoromethylcyclohexanone: $^1$H NMR (CDCl$_3$) δ 0.45–1.16 (m, 15H), 1.92–2.89 (m, 8H); mass spectrum (70 eV) m/z (relative intensity) 267 (19, M-C$_2$H$_5$), 115 (45), 105 (33), 87 (100), 81 (22), 77 (67), 73 (20), 67 (29), 59 (57), 55 (84), 47 (20).

EXAMPLE XLI 9,10-Dihydro-9-hydroxy-10-triethylsiloxy -10-trifluoromethylanthracene A solution of 50 mg (0.13 mmol) of 9,10-dihydro-9-oxo-10-triethylsiloxy-10-trifluoromethylanthracene in 0.5 mL of absolute ethanol was treated successively with 42 mg (0.65 mmol) of zinc dust and 0.5 mL of a solution of 90% acetic acid - 20% water. The mixture was heated to reflux in a 110° C oil bath for 2 hours, allowed to cool to room temperature, and poured into 10 mL of water. The resulting aqueous mixture was extracted with three 5 mL portions of diethyl ether. Combination, drying, and concentration of the ether layers gave a residue which was purified by PTLC (one 1 mm silica gel plate eluted with 50% dichloromethane -50% petroleum ether) to give 34 mg of 87% pure (58% yield) 9,10-dihydro-9-hydroxy-10-triethysiloxy-10-trifluoromethylanthracene as a white solid: mass spectrum (70 eV) m/z (relative intensity) 363 (8, M-C$_2$H$_5$), 211 (100), 183 (21), 77 (25); TMS derivative 466 (M+), 368 (27), 246 (24), 196 (22), 193 (90), 165 (21), 105 (40), 87 (28), 77 (47), 73 (100), 59 (20), 45 (21).

EXAMPLE XLII

4-Hydroxy-4-trifluoromethylcyclohexanone

A solution of 100 mg of 4-hydroxy-4-trifluoromethyl -2,5-cyclohexadien-1-one in 1 mL of absolute ethanol was treated with a few mg of 5% palladium on carbon, hydrogenated in a Parr shaker for one hour under 50 psig of hydrogen, and filtered. Gas chromatographic/-mass spectral analysis indicated that the major component of the filtrate was 4-hydroxy-4-trifluoromethylcyclo hexanone: mass spectrum (70 eV) m/z (relative intensity) 182 (11, M+), 55 (100), 42 (40).

The embodiments of this invention wherein a suitable catalyst together with a proton source are used are illustrated by the following examples.

EXAMPLE XLIII

4-Hydroxy-4-trifluoromethyl-2,5-cyclohexadien-1-one

A mixture of 74 mg (1.3 mmol) of ground ammonium bifluoride (NH$_4$HF$_2$), 119 mg (1.1 mmol) of 1,4-benzoquinone, and 2 mL of acetonitrile was treated with 239 mg (1.3 mmol) of triethyltrifluoromethylsilane and stirred vigorously at room temperature for 4 hours. The mixture was filtered and the filter cake was washed with dichloromethane. Concentration of the combined filtrates gave a black solid which was triturated with dichloromethane. The resulting mixture was filtered and the filter cake was washed with dichloromethane. Concentration of the combined filtrates afforded a brown solid which was purified by PTLC (one 2 mm silica gel plate eluted with a 2% methanol-98% dichloromethane) to give 83 mg (42% yield) of 4-hydroxy-4-tri -fluoromethyl-2,5-cyclohexadien-1-one.

EXAMPLE XLIV 4,6-Di-tert-butyl-2-hydroxy-2-trifluoromethyl -3,5-cyclohexadiene-1-one A mixture of 100 mg (1.7 mmol) of potassium fluoride, 132 mg (0.60 mmol) of 3,5-di-tert-butyl-1,2-benzoquinone, and 2 mL of acetonitrile was treated successively with 40μL (0.70 mmol) of glacial acetic acid and 129 mg (0.70 mmol) of triethyltrifloromethylsilane, and stirred vigorously at room temperature for 15 minutes. The mixture was filtered and the filter cake was washed with dichloromethane. Concentration of the combined filtrates afforded a residue which was purified by PTLC (one 2 mm silica gel plate eluted with 20% dichloromethane - 80% petroleum ether) to give 27 mg (16% yield) of 4,6-di-tert-butyl-2-hydroxy-2-trifluoro -methyl-3,5-cyclohexadiene-one.

EXAMPLE XLV 1,4-Dihydro-4-hydroxy-1-oxo-4-trifluoromethylnaphthalene

A mixture of 74 mg (1.3 mmol) of ground ammonium bifluoride, 174 mg (1.1 mmol) of 1,4-naphthoquinone, and 1 mL of N,N-dimethylformamide was treated with 239 mg (1.3 mmol) of triethyltrifluoromethylsilane and stirred vigorously at room temperature for one hour. Gas chromatographic analysis of the reaction mixture showed that the major naphthalene-desired product was 1,4-dihydro-4-hydroxy-1-oxo-4-trifluoromethylnaphthalene.

The products formed by perfluoroalkylation of ketones, aldehydes and other carbonyl materials pursuant to this invention can be used as intermediates for the synthesis of a variety of perfluoroalkylated alcohols and perfluoroalkylated phenolic compounds which in turn are useful for the synthesis of fluorine-containing phosphite, phosphonate, phosphate, and phosphorothioate esters by known chemistry (e.g. reaction of the perfluoroalkylated alcohol or perfluoroalkylated phenolic compound with PCl$_3$, POCl$_3$, PSCl$_3$, etc. Such fluorine-containing esters of these oxyacids of phosphorus can be used as flame retardants for plastics and polymers such as polystyrene, polyethylene, polypropylene, ABS, etc.; as extreme pressure additives for lubricating oils and greases, and as cutting oil additives for lubricants used in machining operations. Perfluoroalkyl substituted carbinols that can be produced by the process of this invention can be used as solvents and as intermediates for the production of water or oil repellant agents, medicines, agricultural chemicals, dyes, surface active agents, and the like. Also, aliphatic perfluoroalkylated products containing a hydroxyl group on a carbon atom adjacent to another carbon atom containing hydrogen atoms may be subjected to dehydration thereby producing unsaturated bonding. Such unsaturated compounds can be used as monomers in the production of fluorine-containing polymers. See for example U.S. Pat. No. 4,484,993 granted Nov. 27, 1984 to Ishikawa, et al., the disclosure of which is incorporated herein by reference.

This invention is susceptible to considerable variation within the spirit and scope of the appended claims and thus is not intended to be limited by the exemplifications herein provided.

What is claimed is:

1. A process which comprises reacting under substantially anhydrous conditions a perfluoroalkyltrihydrocarbylsilane and a carbonyl compound in the presence of a catalyst such that the carbonyl compound is perfluoroalkylated.

2. A process of claim 1 wherein the catalyst is KF.

3. A process which comprises reacting in the presence of a catalyst and under substantially anhydrous conditions a perfluoroalkyltrihydrocarbylsilane and a carbonyl compound other than a quinone such that the carbonyl compound is perfluoroalkylated.

4. A process of claim 3 wherein the perfluoroalkyltrihydrocarbylsilane is a compound of the formula $CF_3SiR_3$ where R is alkyl or aryl.

5. A process of claim 4 wherein the carbonyl compound is an aldehyde or ketone.

6. A process of claim 5 wherein the carbonyl compound is benzaldehyde.

7. A process of claim 5 wherein the carbonyl compound is cyclohexanone.

8. A process of cliam 5 wherein the carbonyl compound is benzil.

9. A process which comprises reacting in the presence of a catalyst and under substantially anhydrous conditions trifluoromethyltriethylsilane and a carbonyl compound other than a quinone such that the carbonyl compound is perfluoromethylated.

10. A process of claim 9 wherein the carbonyl compound is an aldehyde or ketone.

11. A process of claim 10 wherein the carbonyl compound is benzaldehyde.

12. A process of claim 10 wherein the carbonyl compound is cyclohexanone.

13. A process of claim 10 wherein the carbonyl compound is benzil.

* * * * *